US009864839B2

(12) United States Patent
Baym et al.

(10) Patent No.: US 9,864,839 B2
(45) Date of Patent: Jan. 9, 2018

(54) SYSTEMS, DEVICES, AND METHOD FOR DETERMINING TREATMENT COMPLIANCE INCLUDING TRACKING, REGISTERING, ETC. OF MEDICAL STAFF, PATIENTS, INSTRUMENTATION, EVENTS, ETC. ACCORDING TO A TREATMENT STAGING PLAN

(75) Inventors: Michael H. Baym, Cambridge, MA (US); Ralph G. Dacey, Jr., St. Louis, MO (US); Roy P. Diaz, Seattle, WA (US); Roderick A. Hyde, Redmond, WA (US); Muriel Y. Ishikawa, Livermore, CA (US); Jordin T. Kare, Seattle, WA (US); Eric C. Leuthardt, St. Louis, MO (US); Nathan P. Myhrvold, Medina, WA (US); Dennis J. Rivet, Chesapeake, VA (US); Michael A. Smith, Phoenix, AZ (US); Clarence T. Tegreene, Bellevue, WA (US); Lowell L. Wood, Jr., Bellevue, WA (US); Victoria Y. H. Wood, Livermore, CA (US)

(73) Assignee: EL WHA LLC., Bellevue, WA (US)

( * ) Notice: Subject to any disclaimer, the term of this patent is extended or adjusted under 35 U.S.C. 154(b) by 0 days.

(21) Appl. No.: 13/419,720

(22) Filed: Mar. 14, 2012

(65) Prior Publication Data
US 2013/0240623 A1    Sep. 19, 2013

(51) Int. Cl.
G06K 5/00    (2006.01)
G06F 19/00   (2011.01)
G06Q 50/22   (2012.01)

(52) U.S. Cl.
CPC ........... *G06F 19/325* (2013.01); *G06Q 50/22* (2013.01)

(58) Field of Classification Search
CPC ............................ G06F 19/325; G06Q 50/22
USPC ......................................................... 235/385
See application file for complete search history.

(56) References Cited

U.S. PATENT DOCUMENTS

| 5,919,131 A | 7/1999 | Smoler et al. |
| 6,047,259 A | 4/2000 | Campbell et al. |
| 6,671,540 B1 * | 12/2003 | Hochman ............ A61B 5/0059 600/431 |
| 7,032,752 B2 | 4/2006 | Krackow |
| 7,389,928 B2 | 6/2008 | Lubow |

(Continued)

OTHER PUBLICATIONS

"Joint Commission Center for Transforming Healthcare Aims to Reduce the Risk of Wrong Site Surgery"; Yahoo! Finance; bearing a date of Jun. 29, 2011; pp. 1-4; Yahoo! Inc.

(Continued)

*Primary Examiner* — Laura Gudorf
(74) *Attorney, Agent, or Firm* — Fogg & Powers LLC

(57) ABSTRACT

Systems, devices, and methods are described for tracking, registering, etc. of medical staff, patients, instrumentation, events, or the like according to a treatment staging plan. For example a medical apparatus includes a right-patient verification device having an interrogation interface device that elicits at least one of identification data, authorization data, or treatment plan data from a medical procedure authorization device associated with a patient; and a right-site verification device that generates patient-specific treatment staging data consistent with the at least one of the identification data, the authorization data, or the treatment plan data.

40 Claims, 6 Drawing Sheets

(56) References Cited

U.S. PATENT DOCUMENTS

| | | | |
|---|---|---|---|
| 7,447,643 | B1 | 11/2008 | Olson et al. |
| 7,540,287 | B2 | 6/2009 | Chole |
| 7,833,219 | B2 | 11/2010 | Tashiro et al. |
| 7,868,754 | B2* | 1/2011 | Salvat, Jr. ............... 340/539.13 |
| 8,177,064 | B2* | 5/2012 | McCormick et al. ........ 206/370 |
| 2002/0075201 | A1 | 6/2002 | Sauer et al. |
| 2003/0182815 | A1 | 10/2003 | Carlson, II |
| 2003/0184081 | A1 | 10/2003 | Carlson, II |
| 2003/0187458 | A1 | 10/2003 | Carlson, II |
| 2005/0102167 | A1* | 5/2005 | Kapoor ............................. 705/3 |
| 2005/0228256 | A1 | 10/2005 | Labadie et al. |
| 2006/0096877 | A1 | 5/2006 | Khajavi et al. |
| 2006/0124493 | A1 | 6/2006 | Krackow |
| 2006/0235488 | A1* | 10/2006 | Nycz et al. ...................... 607/60 |
| 2007/0018810 | A1* | 1/2007 | Smythe et al. .......... 340/539.12 |
| 2007/0027459 | A1 | 2/2007 | Horvath et al. |
| 2007/0129991 | A1 | 6/2007 | Kuo |
| 2007/0186923 | A1* | 8/2007 | Poutiatine et al. ...... 128/200.14 |
| 2007/0210923 | A1* | 9/2007 | Butler et al. ............... 340/572.8 |
| 2007/0273517 | A1* | 11/2007 | Govind ...................... 340/572.1 |
| 2008/0018469 | A1* | 1/2008 | Volpi et al. ................ 340/572.1 |
| 2008/0030345 | A1* | 2/2008 | Austin et al. .............. 340/572.8 |
| 2008/0068197 | A1* | 3/2008 | Neubauer et al. ......... 340/686.1 |
| 2008/0126122 | A1* | 5/2008 | Warner et al. .................... 705/2 |
| 2008/0257961 | A1 | 10/2008 | Lubow |
| 2008/0281254 | A1* | 11/2008 | Humayun et al. .............. 604/22 |
| 2009/0018864 | A1 | 1/2009 | Gecelter |
| 2009/0043253 | A1 | 2/2009 | Podaima |
| 2009/0267765 | A1* | 10/2009 | Greene et al. ............. 340/568.1 |
| 2009/0317002 | A1* | 12/2009 | Dein ............................. 382/224 |
| 2010/0001838 | A1* | 1/2010 | Miodownik et al. ........ 340/10.1 |
| 2010/0049756 | A1 | 2/2010 | Chemitiganti et al. |
| 2010/0057059 | A1 | 3/2010 | Makino |
| 2010/0082368 | A1* | 4/2010 | Gecelter et al. ................... 705/3 |
| 2010/0134257 | A1* | 6/2010 | Puleston et al. ............. 340/10.4 |
| 2010/0183199 | A1 | 7/2010 | Smith et al. |
| 2010/0204999 | A1 | 8/2010 | Scarola |
| 2010/0262433 | A1 | 10/2010 | Kreiner et al. |
| 2011/0029320 | A1 | 2/2011 | Jamali et al. |
| 2011/0106561 | A1 | 5/2011 | Eaton, Jr. et al. |
| 2011/0137680 | A1 | 6/2011 | Sweeney |
| 2013/0218137 | A1* | 8/2013 | Abovitz ................. A61B 19/22 606/1 |
| 2014/0031668 | A1* | 1/2014 | Mobasser et al. ............. 600/409 |

OTHER PUBLICATIONS

Paquin et al.; "Multiscale Image Registration"; Mathematical Biosciences and Engineering; bearing a date of Jan. 26, 2006; pp. 389-418; vol. 3, No. 2.

Paquin et al.; "Multiscale registration of planning CT and daily cone beam CT images for adaptive radiation therapy"; Med. Phys.; bearing dates of Dec. 4, 2008 and Jan. 2009; pp. 4-11; vol. 36, No. 1; Am. Assoc. Phys. Med.

Zitová et al.; "Image registration methods: a survey"; Image and Vision Computing, Elsevier; bearing a date of Jun. 26, 2003; pp. 977-1000; vol. 21; Elsevier B.V.

PCT International Search Report; International App. PCT/US13/29889; May 13, 2013; pp. 1-2.

Chou et al.; "Augmented Reality Based Preoperative Planning for Robot Assisted Tele-neurosurgery"; IEEE International Conference on Systems, Man and Cybernetics; Oct. 10, 2004; pp. 2901-2906; IEEE.

European Search Report; European App. No. EP 13 76 1397; Sep. 25, 2015 (received by our Agent on Sep. 29, 2015); pp. 1-6.

\* cited by examiner

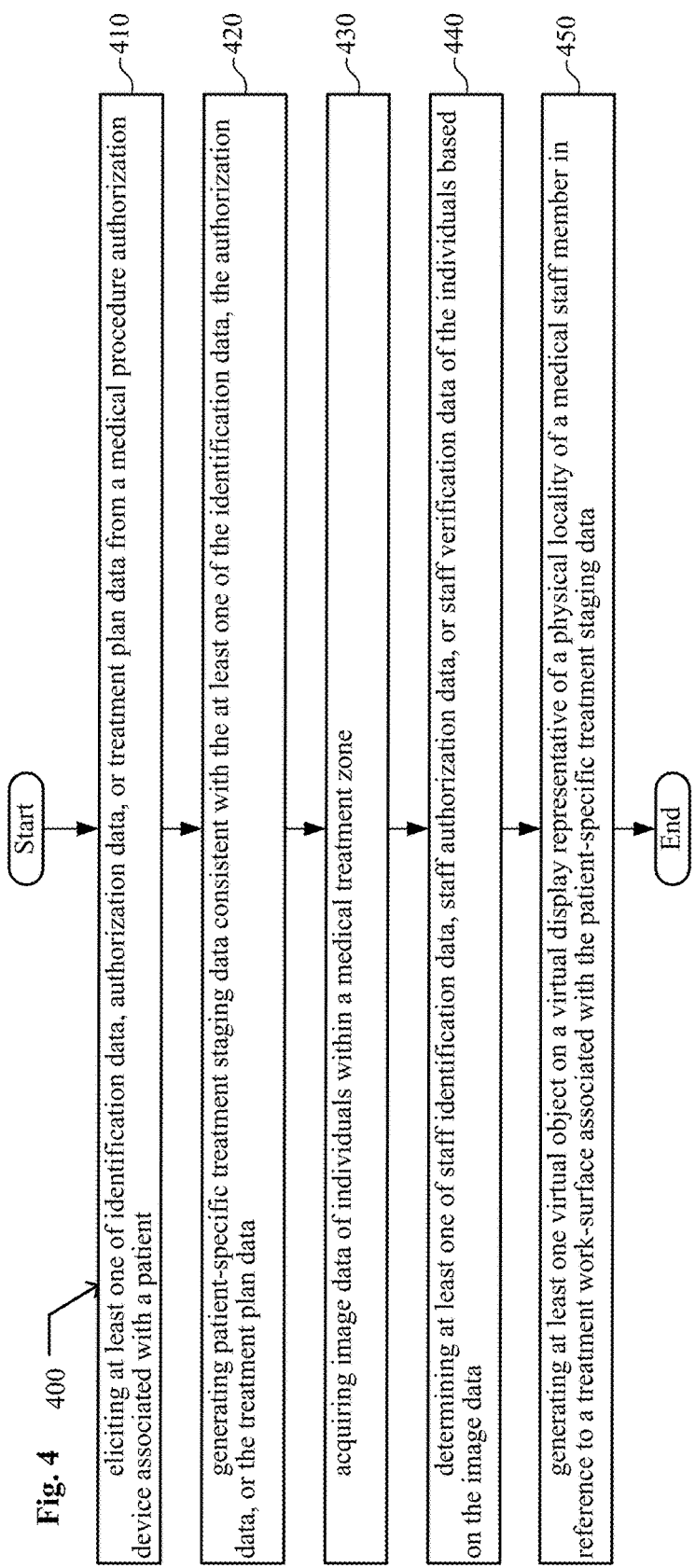

Fig. 4 400

410 — eliciting at least one of identification data, authorization data, or treatment plan data from a medical procedure authorization device associated with a patient 420 — generating patient-specific treatment staging data consistent with the at least one of the identification data, the authorization data, or the treatment plan data 430 — acquiring image data of individuals within a medical treatment zone 440 — determining at least one of staff identification data, staff authorization data, or staff verification data of the individuals based on the image data 450 — generating at least one virtual object on a virtual display representative of a physical locality of a medical staff member in reference to a treatment work-surface associated with the patient-specific treatment staging data

_____ bearing one or more instructions for establishing surgery room staff staging data consistent with the treatment plan for the patient.

one or more instructions for establishing treatment instrumentation staging data consistent with the treatment plan for the patient one or more instructions for generating a virtual representation of the medical apparatus in a virtual space corresponding to the physical location of the medical apparatus respective to a treatment work-surface location one or more instructions for generating one or more cryptographic keys, based on the surgery room staff staging data, which provide authorization to the medical apparatus to initiate treatment one or more instructions for detecting the presence and identity of at least one operating theater staff member.

one or more instructions for determining the physical location of the operating theater staff member relative to a treatment work-surface one or more instructions for registering the physical location of the operating theater staff member relative to the treatment work-surface one or more instructions for registering a treatment staging position location with the physical location of the operating theater staff member based on patient specific treatment staging data one or more instructions for detecting the presence and identity of at least one treatment instrument one or more instructions for determining the physical location of the treatment instrument relative to the treatment work-surface one or more instructions for registering the physical location of the treatment instrument relative to the treatment work-surface

Fig. 5B

502 one or more instructions for registering a treatment staging position location with the physical location of the treatment instrument based on patient specific treatment staging data one or more instructions for registering a patient location with the physical location of the treatment instrument based on patient specific treatment staging data.

one or more instructions for telemetrically acquiring at least one of identification data, authorization data, or treatment plan data from a medical procedure authorization device associated with a patient one or more instructions for generating patient-specific treatment staging data one or more instructions for acquiring image data of individuals within a medical treatment zone one or more instructions for determining at least one of staff identification data, staff authorization data, or staff verification data of the individuals based on the image data one or more individuals within the medical treatment zone in reference to a medical treatment zone based on the image data one or more instructions for generating a virtual representation of the locality of the one or more individuals within the medical treatment zone on a virtual display based on at least one of the staff identification data, the staff authorization data, or the staff verification data

SYSTEMS, DEVICES, AND METHOD FOR DETERMINING TREATMENT COMPLIANCE INCLUDING TRACKING, REGISTERING, ETC. OF MEDICAL STAFF, PATIENTS, INSTRUMENTATION, EVENTS, ETC. ACCORDING TO A TREATMENT STAGING PLAN

SUMMARY

In an aspect, the present disclosure is directed to, among other things, a medical apparatus including a right-patient verification device and a right-site verification device. In an embodiment, the right-patient verification device includes an interrogation interface device configured to elicit at least one of identification data, authorization data, or treatment plan data from a medical procedure authorization device associated with a patient (e.g., worn, attached, implanted, etc.). In an embodiment, the right-site verification device is configured to generate patient-specific treatment staging data consistent with the at least one of the identification data, the authorization data, or the treatment plan data.

In an aspect, the present disclosure is directed to, among other things, a medical procedure monitoring system including a right-patient verification device and a right-staff verification device. In an embodiment, the right-patient verification device is configured to acquire at least one of identification data, authorization data, or treatment plan data from a patient-specific medical procedure authorization device associated with a patient under test. In an embodiment, the right-patient verification device is configured to generate patient-specific treatment staging data (e.g., treatment staff work-region data, operation room staff work-region data, patient treatment locality data, registration data, treatment plan assignment data, treatment work-surface locality data, treatment work-surface locality data, work-zone staging registration data, staff location within a medical treatment work-zone, or the like). In an embodiment, the right-staff verification device is configured to acquire image data of individuals within a medical treatment work-zone (e.g., a surgery room, a provider locality, a treatment locality, an outpatient facility, treatment facility, etc.) and to determine at least one of identity, authorization status, role in treatment plan, or the like based on the image data. In an embodiment, the right-staff verification device is configured to generate patient-specific staff staging data in agreement with a treatment plan data, a patient-specific treatment protocol, a standard treatment or protocol, or the like.

In an aspect, the present disclosure is directed to, among other things, a medical system including a right-site verification device, a right-object inventory device, and an object tracking system. In an embodiment, the right-site verification device is configured to generate work-zone staging registration data associated with at least one of a patient treatment locality, an operation room staff work-region, or a treatment work-surface locality. In an embodiment, the right-object inventory device is configured to determine at least one of treatment object identification data, treatment object location data, or treatment object operational data based on the work-zone staging registration data. In an embodiment, the object tracking system is configured to update, in real time, a treatment object virtual location in a virtual space corresponding to the physical location of the treatment object in a physical operation room work-region.

In an aspect, the present disclosure is directed to, among other things, a right-patient, right-procedure, verification method. In an embodiment, the method includes eliciting at least one of identification data, authorization data, or treatment plan data from a medical procedure authorization device associated with a patient. In an embodiment, the method includes generating patient-specific treatment staging data consistent with the at least one of the identification data, the authorization data, or the treatment plan data. For example, in an embodiment, the medical procedure authorization device associated with a patient is interrogated to elicit an authorization key. Upon authorization, patient-specific treatment staging data such as pre-treatment, treatment, or post-treatment staging data (for locating or tracking staff, patient, treatment instruments, etc.) is generated according to an established patient-specific treatment staging protocol. In an embodiment, once identified and located, the method includes tracking staff, patients, treatment instruments, events, or the like to determine a compliance status based on the patient-specific treatment staging data.

In an aspect, the present disclosure is directed to, among other things, a medical system including a work-volume registration system. In an embodiment, the work-volume registration system is configured to track translation of a work-volume associated with a medical practitioner. In an embodiment, the working volume comprises a three-dimensional physical region bounded proximally by the body of the medical practitioner and distally by the arc swept by the fingertips of one or both hands with a range of elbow flexion or body rotations about its vertical axis. In an embodiment, the working volume comprises a physical region bounded proximally by a proximal reach of the medical practitioner and by the distal boundary in any direction which the medical practitioner can attain by any combination of postures, rotations, flexion movements, or extension movements. In an embodiment, the working volume comprises a region defined by a range of motions consistent with a treatment staging plan. In an embodiment, the working volume comprises a region defined by the reach of the medical practitioner. In an embodiment, the work-volume registration system is configured to determine proximity of the work-volume to at least one treatment work-zone location (e.g., work-zone location, work-surface location, instrument operation station, medical apparatus station, surgery site, treatment focal region, treatment region, surgical instrument station location, medical apparatus operation station, medical instrument location, etc.) associated with a treatment staging plan. In an embodiment, the work-volume registration system is configured to track translation of a work-volume associated with a medical practitioner and to determine a treatment staging plan compliance status.

In an aspect, the present disclosure is directed to, among other things, a system including a real-time registration device and a right-site verification device. In an embodiment, the real-time registration device is configured to register at least one work-volume associated with a medical practitioner with at least one treatment work-zone and to generate work-zone registration information. In an embodiment, the real-time registration device is configured to locate, register, and track at least one work-volume associated with a medical practitioner with at least one treatment work-zone and to generate work-zone registration information. In an embodiment, the right-site verification device includes one or more computing devices that compare the generated work-zone registration information to patient-specific treatment staging data associated with a patient under treatment. In an embodiment, the right-site verification device includes one or more computing devices that compare the generated work-zone registration information to patient-specific treatment staging data associated with a patient under treatment and determine a treatment staging plan compliance status.

In an aspect, the present disclosure is directed to, among other things, a medical system including a right-staff verification device. In an embodiment, the right-staff verification device is configured to acquire image data of individuals within a medical treatment work-zone. In an embodiment, the right-staff verification device is configured to determine at least one of staff identification data, staff authorization data, or staff verification data of the individuals based on the image data. In an embodiment, the right-staff verification device is configured to generate patient-specific staff staging data. In an embodiment, the right-staff verification device is configured to track translation of at least one of an eye location or a hand location of at least one individual. In an embodiment, the right-staff verification device is configured to determine proximity of the hand location or the eye location to at least one treatment work-surface location. In an embodiment, the right-staff verification device is configured to acquire image data of individuals within a medical treatment work-zone and determine a treatment plan compliance status based on the acquire image data.

In an aspect, the present disclosure is directed to, among other things, a medical system including a right-staff image recognition system and a right-treatment object inventory recognition system. In an embodiment, the right-staff image recognition system is configured to identify groups of pixels indicative of one or more individuals within a medical treatment work-zone in the digital image, and to generate one or more connected components of a graph representative of groups of pixels indicative of an identity, locality, job duty, treatment plan assignment, etc., of the one or more individuals imaged in the at least one digital image. In an embodiment, the right-treatment object inventory recognition system is configured to identify groups of pixels indicative of one or more objects associated with a medical treatment plan and imaged in the at least one digital image, and to generate one or more connected components of a graph representative of groups of pixels indicative of an identity, locality, etc., of the one or more objects within the medical treatment work-zone and imaged in the at least one digital image.

In an aspect, the present disclosure is directed to, among other things, a medical procedure authorization device including a telematic right-site and right-patient verification device having one or more memory devices and a telematic interface. In an embodiment, the medical procedure authorization device includes one or more memory devices having patient-specific treatment staging data and at least one of patient-specific identification data, patient-specific authorization data, or patient-specific treatment plan data stored thereon. In an embodiment, the medical procedure authorization device includes a telematic interface operable to communicate patient-specific treatment staging data and at least one of the patient-specific identification data, the patient-specific authorization data, or the patient-specific treatment plan data. In an embodiment, the medical procedure authorization device includes a telematic interface operable to communicate a treatment plan compliance status.

In an aspect, the present disclosure is directed to, among other things, a computer program product including a non-transitory signal-bearing medium bearing one or more instructions for detecting the presence and identity of at least one operating theater staff member. In an embodiment, the computer program product includes a non-transitory signal-bearing medium bearing one or more instructions for determining the physical location of the operating theater staff member relative to a treatment work-surface. In an embodiment, the computer program product includes a non-transitory signal-bearing medium bearing one or more instructions for registering the physical location of the operating theater staff member relative to one or more treatment work-surfaces. In an embodiment, the computer program product includes a non-transitory signal-bearing medium bearing one or more instructions for determining a measure of treatment plan compliance based on the registration of the physical location of the operating theater staff member relative to the treatment work-surface.

In an aspect, the present disclosure is directed to, among other things, a right-site, right-patient, determination system including a real-time object and participant-recognition device. In an embodiment, the real-time object and participant-recognition device includes an optical recognition distributed sensor network that determines identity data associated with one or more participants within a medical treatment zone and determines one or more of identity, location, position, or movement of a body portion of the one or more participants. In an embodiment, the real-time object and participant-recognition device includes an optical recognition distributed sensor network that determines treatment plan compliance data based on the identity data associated with one or more participants. In an embodiment, the real-time object and participant-recognition device includes an optical recognition distributed sensor network that determines treatment plan compliance data based on the location data associated with one or more participants or treatment instruments within a medical treatment zone. In an embodiment, the real-time object and participant-recognition device includes an optical recognition distributed sensor network that determines treatment plan compliance data based on one or more of the identity, location, position, or movement of a body portion of the one or more participants.

In an aspect, the present disclosure is directed to, among other things, a right-site, and a right-patient determination system using real-time automatic image recognition system including a real-time object recognition device. In an embodiment, the real-time object recognition device is configured to identify groups of pixels indicative of one or more patient landmarks imaged in the at least one digital image according to a treatment staging plan. In an embodiment, the real-time object recognition device is configured to generate one or more connected components of a graph representative of groups of pixels indicative of the one or more one or more patient landmarks imaged in the at least one digital image. In an embodiment, the real-time object recognition device is configured to generate patient landmarks dynamics data indicative of at least one of a patient landmark position, patient landmark angle, patient landmark direction, patient landmark force, patient landmark contact, patient landmark pressure, patient landmark speed, patient landmark altitude, or patient landmark acceleration, or any combination thereof. In an embodiment, the real-time object recognition device is configured to generate a treatment staging compliance status based at least one patient landmark imaged in the at least one digital image.

In an aspect, the present disclosure is directed to, among other things, a computer program product including a non-transitory signal-bearing medium bearing one or more instructions for telemetrically acquiring at least one of identification data, authorization data, or treatment plan data from a medical procedure authorization device associated with a patient. In an embodiment, the computer program product includes a non-transitory signal-bearing medium bearing one or more instructions for generating patient-specific treatment staging data based on one or more of the identification data, authorization data, or treatment plan data. In an embodiment, the computer program product includes a non-transitory signal-bearing medium bearing one or more instructions for acquiring image data of individuals within a medical treatment work-zone. In an embodiment, the computer program product includes a non-transitory signal-bearing medium bearing one or more instructions for determining at least one of staff identification data, staff authorization data, or staff verification data of the individuals based on the image data.

In an embodiment, the computer program product includes a non-transitory signal-bearing medium bearing one or more instructions for determining a treatment staging compliance status based on the image data. In an embodiment, the computer program product includes a non-transitory signal-bearing medium bearing one or more instructions for determining a locality of one or more individuals within the medical treatment work-zone in reference to a medical treatment work-zone based on the image data. In an embodiment, the computer program product includes a non-transitory signal-bearing medium bearing one or more instructions for generating a virtual representation of the locality of the one or more individuals or one or more treatment instruments, or combinations thereof, within the medical treatment work-zone on a virtual display based on at least one of the staff identification data, the staff authorization data, or the staff verification data. In an embodiment, the computer program product includes a non-transitory signal-bearing medium bearing one or more instructions for locating and tracking a locality of one or more individuals within the medical treatment work-zone and displaying a treatment staging compliance status based on the location and translation of the one or more individuals within the medical treatment work-zone. In an embodiment, the computer program product includes a non-transitory signal-bearing medium bearing one or more instructions for generating a virtual display indicative of a treatment staging compliance status.

BRIEF DESCRIPTION OF THE FIGURES

FIG. 4 shows a flow diagram of a method according to one embodiment.

FIGS. 5A and 5B show a flow diagram of a computer program product according to one embodiment.

DETAILED DESCRIPTION

Figure 1:
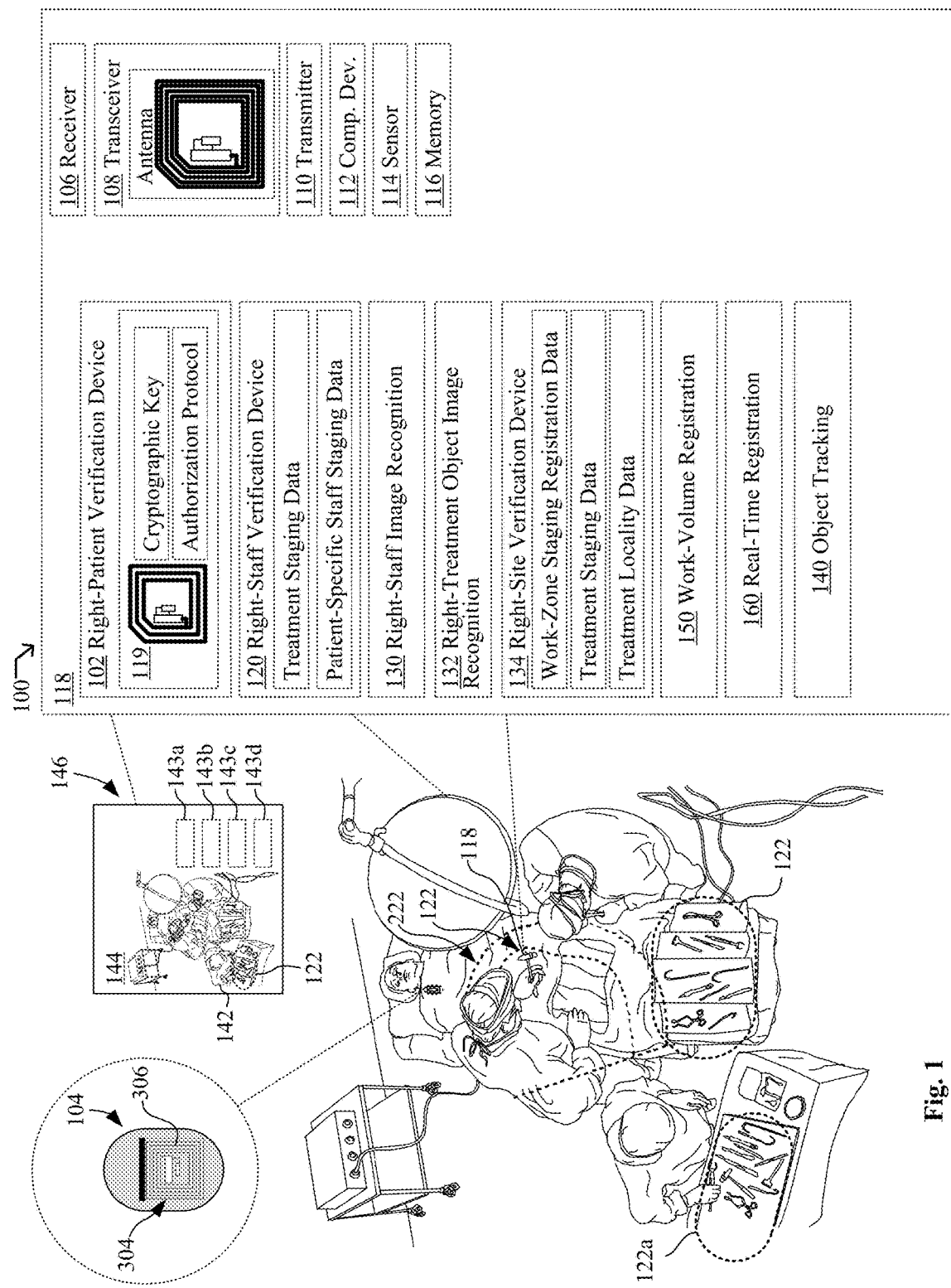
FIG. 1 is a perspective view of a system including a right-patient verification device according to one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 shows a system 100 (e.g., a medical system, a medical procedure monitoring system, a medical procedure authorization system, a right-patient verification system, a right-staff verification system, a right-procedure verification system, a right-site determination system, a right-patient determination system, or the like) in which one or more methodologies or technologies can be implemented such as, for example, assessing treatment compliance, determining a level of adherence or compliance to a treatment staging plan, assessing compliance with practice treatment guidelines, determining a treatment staging plan, orchestrating a treatment plan, determining a treatment staging compliance status, arranging or directing the elements of a treatment protocol, or the like.

In an embodiment, the system 100 includes a right-patient verification device 102. In an embodiment, during operation, the right-patient verification device 102 communicates with a medical procedure authorization device 104 and acquires one or more of identification data, authorization data, or treatment plan data. In an embodiment, the right-patient verification device 102 generates patient-specific treatment staging data consistent with the patient's treatment plan determined from one or more of the identification data, authorization data, or treatment plan data. For example, in an embodiment, during operation, the right-patient verification device 102 generates one or more of needed staff data, medical treatment instrument inventory data, pre-operative protocol data, post-operative protocol data, location of staff or medical treatment instruments during treatment data, data related to the right baby in cases of a c-section, parent or guardian data when patient is a minor, etc.

In an embodiment, the system 100 includes a right-patient verification device 102 that is configured to acquire at least one of identification data, authorization data, or treatment plan data from a medical procedure authorization device 104 associated with a patient. For example, in an embodiment, the right-patient verification device 102 includes at least one of a receiver 106, transceiver 108, or transmitter 110 operable to communicate with the medical procedure authorization device 104 associated with a patient and to acquire at least one of identification data, authorization data, or treatment plan data. In an embodiment, the right-patient verification device 102 includes circuitry configured to, for example, elicit at least one of identification data, authorization data, or treatment plan data from a medical procedure authorization device 104 associated with a patient. For example, in an embodiment, the right-patient verification device 102 includes at least one of a receiver 106, transceiver 108, or transmitter 110 that elicits one or more cryptographic keys from the medical procedure authorization device 104 associated with a patient. In an embodiment, the right-patient verification device 102 includes circuitry configured to implement a discovery and a registration protocol that allows, for example, a medical apparatus 118 (e.g., a surgical tool, surgical instrument, diagnostic equipment, support equipment, or the like) and a medical procedure authorization device 104 to find each other and initiate authorization protocols (e.g., protocols that negotiate one or more pre-shared keys, public key certificate-based authentication protocols, internet protocol security authentication methods, etc.).

In an embodiment, circuitry includes, among other things, one or more computing devices 112 such as a processor (e.g., a microprocessor), a central processing unit (CPU), a digital signal processor (DSP), an application-specific integrated circuit (ASIC), a field programmable gate array (FPGA), or the like, or any combinations thereof, and can include discrete digital or analog circuit elements or electronics, or combinations thereof. In an embodiment, circuitry includes one or more ASICs having a plurality of predefined logic components. In an embodiment, circuitry includes one or more FPGA having a plurality of programmable logic components.

In an embodiment, the right-patient verification device 102 includes circuitry having one or more components operably coupled (e.g., communicatively, electromagnetically, magnetically, ultrasonically, optically, inductively, electrically, capacitively coupled, or the like) to each other. In an embodiment, circuitry includes one or more remotely located components. In an embodiment, remotely located components are operably coupled via wireless communication. In an embodiment, remotely located components are operably coupled via one or more receivers 106, transceivers 108, or transmitters 110, or the like.

In an embodiment, circuitry includes one or more memory devices 116 that, for example, store instructions or data. For example, in an embodiment, the right-patient verification device 102 includes one or more memory devices 116 that store patient-specific treatment staging data, patient-specific identification data, patient-specific authorization data, or patient-specific treatment plan data. Non-limiting examples of one or more memory devices 116 include volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like), persistent memory, or the like. Further non-limiting examples of one or more memory devices 116 include Erasable Programmable Read-Only Memory (EPROM), flash memory, or the like. The one or more memory devices 116 can be coupled to, for example, one or more computing devices 112 by one or more instructions, data, or power buses. In an embodiment, the right-patient verification device 102 includes one or more memory devices 116 that, for example, store needed staff data, medical treatment instrument inventory data, pre-operative protocol data, post-operative protocol data, location of staff data, location of medical treatment instruments during treatment data, or the like. In an embodiment, the right-patient verification device 102 includes one or more memory devices 116 that, for example, store object tracking data, work-zone staging registration data, or the like.

In an embodiment, circuitry includes one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In an embodiment, circuitry includes one or more user input/output components that are operably coupled to at least one computing device to control (electrical, electromechanical, software-implemented, firmware-implemented, or other control, or combinations thereof) at least one parameter associated with, for example, In an embodiment, circuitry includes a computer-readable media drive or memory slot that is configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as a magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., receiver 106, transceiver 108, or transmitter 110, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

In an embodiment, the right-patient verification device 102 includes circuitry having one or more modules optionally operable for communication with one or more input/output components that are configured to relay user output and/or input. In an embodiment, a module includes one or more instances of electrical, electromechanical, software-implemented, firmware-implemented, or other control devices. Such devices include one or more instances of memory, computing devices 112, antennas, power or other supplies, logic modules or other signaling modules, gauges or other such active or passive detection components, piezoelectric transducers, shape memory elements, micro-electromechanical system (MEMS) elements, or other actuators.

In an embodiment, the right-patient verification device 102 includes one or more sensors 114 operable to detect (e.g., assess, calculate, evaluate, determine, gauge, measure, monitor, quantify, resolve, sense, or the like) a medical procedure authorization device 104 associated with a patient. Non-limiting examples of sensors 114 include acoustic sensors, optical sensors, electromagnetic energy sensors, image sensors, photodiode arrays, charge-coupled devices (CCDs), complementary metal-oxide-semiconductor (CMOS) devices, transducers, optical recognition sensors, infrared sensors, radio frequency components sensors, thermo sensor, or the like. In an embodiment, the right-patient verification device 102 includes one or more transducers that detect and convert acoustic signals emitted from the medical procedure authorization device 104 associated with a patient into electronic signals.

In an embodiment, the system 100 includes a right-patient verification device 102 configured to generate patient-specific treatment staging data. For example, in an embodiment, the system 100 includes a right-patient verification device 102 configured to one or more of object identification data, object location data, treatment protocol data, staff member location data, patient location data, medical instruments location data, medical apparatuses inventory data, treatment planning data, or the like. In an embodiment, in the case were multiple patients are undergoing concurrent or inter-related procedures (e.g., organ transplants, etc.) the right-patient verification device 102 is configured to generate patient-specific treatment staging data for each patient taking part in the procedure. In an embodiment, the system 100 includes a right-patient verification device 102 configured to generate health record data.

In an embodiment, the right-patient verification device 102 is configured to determine patient identification by facial recognition. For example, in an embodiment, the right-patient verification device 102 includes circuitry, such as, one or more sensor 114 (e.g., optical sensors, cameras, radiofrequency sensors, three-dimensional sensors (e.g., 3-D sensors operable to capture information about the shape of a face, etc.) or the like) operable to acquire image data. In an embodiment, during operation, the right-patient verification device 102 determines an individual's identity by detecting and analyzing distinct features of an individual's face surface (e.g., structural features of the eye sockets, chin, nose, etc.). In an embodiment, the right-patient verification device 102 comprises three-dimensional sensor-based face recognition modalities. For example, in an embodiment, the right-patient verification device 102 includes one or more infrared light sensor operable to measures depth, position, motion, or the like. In an embodiment, the right-patient verification device 102 comprises a multimodal biometric sensor for identifying persons, object, or the like.

In an embodiment, the right-patient verification device 102 is configured to determine patient identification based on an image of at least one of an anatomical target, a biological structure, an artificial surface marking, a tattoo, a plurality of nanoparticle fiducial markers, or the like. For example, in an embodiment, the right-patient verification device 102 detects and tracks at least one of an anatomical target, a biological structure, an artificial surface marking, a tattoo, a plurality of nanoparticle fiducial markers, or the like to determine patient identification data, treatment staging plan compliance status data, or the like. In an embodiment, the right-patient verification device 102 includes a plurality of sensors 114 that actively detect, track, or monitor one or more anatomical targets, biological structures, artificial surface markings, tattoos, nanoparticle fiducial markers, or the like.

In an embodiment, the right-patient verification device 102 portion of the medical apparatus 118 communicates with a medical procedure authorization device 104 and acquires one or more of identification data, authorization data, or treatment plan data to determine a treatment staging plan. The right-patient verification device 102 then compares time series treatment delivery data (e.g., time delay data associated with the delivery of a contrast agent before an imaging procedure, the onset of an effect of a drug, duration of drug delivery, or the like) to the treatment staging plan to determine a compliance status. In an event that the compliance status is indicative of a non-compliance event, in an embodiment, the medical apparatus 118 is deactivated, a procedure is modified, delayed, or terminated, a new treatment protocol is generated, or the like.

In an embodiment, the medical apparatus 118 is configured to determine a compliance status based on treatment staging data. For example, in an embodiment, the medical apparatus 118 is configured to track staff, patients, treatment instruments, events, or the like to determine a compliance status based on the patient-specific treatment staging data. In an embodiment, during operation, the medical apparatus 118 determines a compliance status based on a detected series of events as they corresponded to a patient-specific treatment staging data. For example, in an embodiment, the medical apparatus 118 determines a compliance status based on events associated with a treatment timeline (e.g., a schedule, chronology, timeline, etc., for an organ transplant, joint replacement, dental and surgical treatment for a procedure, imaging treatment, multi-patient treatment, or the like.). For example, in an embodiment, during operation, the right-patient verification device 102 portion of the medical apparatus 118 communicates with a medical procedure authorization device 104 and acquires one or more of identification data, authorization data, or treatment plan data to determine a treatment staging plan. The right-patient verification device 102 then compares time series treatment delivery data (e.g., time delay data associated with the delivery of a contrast agent before an imaging procedure, the onset of an effect of a drug, duration of drug delivery, or the like) to the treatment staging plan to determine a compliance status. In an event that the compliance status is indicative of a non-compliance event, in an embodiment, the medical apparatus 118 is deactivated, a procedure is modified, delayed, or terminated, a new treatment protocol is generated, or the like.

In an embodiment, the right-patient verification device 102 is configured to detect preparation to act on a body part or action in progress. For example, in an embodiment, the right-patient verification device 102 is configured to detect exposure of a body part (e.g., via a markings or indicators that are revealed upon exposure of the body part, etc.). In an embodiment, the right-patient verification device 102 is configured to detect application of antiseptic or sterilants in preparation for surgery (e.g., before patient is obscured by drape).

In an embodiment, a system 100 includes a medical apparatus 118 having a right-patient verification device 102. In an embodiment, the medical apparatus 118 includes a right-patient verification device 102 having an interrogation interface device 119 configured to elicit at least one of identification data, authorization data, or treatment plan data from a medical procedure authorization device 104 associated with a patient. In an embodiment, the right-patient verification device 102 is configured to wirelessly elicit and detect an authorization signal from the medical procedure authorization device 104. For example, in an embodiment, the right-patient verification device 102 includes at least one receiver 106, transceiver 108, or transmitter 110 operable to elicit and detect an authorization signal from the medical procedure authorization device 104.

In an embodiment, the medical apparatus 118 operates in a networked environment using logical connections to one or more remote computing devices 112 (e.g., a common network node, a network computer, a network node, a peer device, a personal computer, a router, a server, a tablet PC, a tablet, etc.) and typically includes many or all of the elements described above. In an embodiment, the logical connections include connections to a local area network (LAN), a wide area network (WAN), and/or other networks. In an embodiment, the logical connections include connections to one or more enterprise-wide computer networks, intranets, and the Internet. In an embodiment, the system 100, the medical apparatus 118, or the like operate in a cloud computing environment including one or more cloud computing systems (e.g., private cloud computing systems, public cloud computing systems, hybrid cloud computing systems, or the like).

In an embodiment, the right-patient verification device 102 is responsive based on at least one of an authorization protocol, an authentication protocol, an activation protocol, a negotiation protocol, or the like. For example, during operation, in an embodiment, the system 100 implements a discovery and a registration protocol that allows the medical procedure authorization device 104 and the medical apparatus 118 to find each other and negotiate one or more pre-shared keys. This negotiation is implemented using a variety of technologies, methodologies, and modalities including, for example, using aggressive-mode exchanges, main-mode exchanges, quick-mode exchanges, or combinations thereof. In an embodiment, the system is operable to establish an Internet Security Association and Key Management Protocol (ISAKMP) security association (SA), between allows medical procedure authorization device 104 and the right-patient verification device 102 using one or more negotiations schemas. Non-limiting examples of negotiation types include aggressive-mode negotiation, main-mode negotiation, quick-mode negotiation, or the like. Further limiting examples of negotiation types include aggressive mode negotiation using pre-shared key authentication followed by quick-mode negotiation, aggressive mode using digital signature authentication followed by quick-mode negotiation, main mode negotiation using digital signature authentication followed by quick-mode negotiation, main mode negotiation using encrypted nonces authentication followed by quick-mode negotiation, main mode negotiation using pre-shared key authentication followed by quick-mode negotiation, or the like. In an embodiment, the ISAKMP SA is used to protect subsequent key exchanges between peer devices (e.g., via quick-mode negotiation protocols, etc.).

In an embodiment, the right-patient verification device 102 includes at least one acoustic energy transmitter or electromagnetic energy transmitter. In an embodiment, the right-patient verification device 102 includes at least one wireless transmitter. In an embodiment, the right-patient verification device 102 includes at least one antenna. For example, in an embodiment, the right-patient verification device 102 includes at least one bistatic antenna. In an embodiment, the right-patient verification device 102 includes at least one of a carrier waveform selective interrogation interface or a frequency selective interrogation interface. In an embodiment, the right-patient verification device 102 includes at least one of an acoustic energy selective interrogation interface or an electromagnetic energy selective interrogation interface. In an embodiment, the right-patient verification device 102 is operable to emit at least one of electromagnetic energy in the radio frequency range or acoustic energy in the ultrasonic frequency range.

In an embodiment, the system 100 includes a right-staff verification device 120. In an embodiment, the system 100 includes a right-staff verification device 120 configured to acquire image data of individuals within a medical treatment work-zone. For example, during operation, the right-staff verification device 120 determines the identity of one or more individuals within a medical treatment work-zone by detecting and analyzing distinct physical features of the individual's face. In an embodiment, the system 100 includes a right-staff verification device 120 configured to determine at least one of staff identification data, staff authorization data, or staff verification data of the individuals based on the image data. In an embodiment, during operation, the right-staff verification device 120 determines the identity of one or more individuals within a medical treatment work-zone using three-dimensional sensor-based face recognition modalities.

In an embodiment, the system 100 includes a right-staff verification device 120 configured to generate patient-specific staff staging data. For example, in an embodiment, once the identity of the patient is determined, the right-staff verification device 120 is configured to generate staff staging data indicative of the type of staffing need for the instant treatment; the location of staff, instruments, patient, apparatus, etc.; the placement of individuals within a medical treatment work-zone, the work surface 122 locations consistent with the instant treatment, the work zone locations consistent, tracking position of objects (medical instruments, individuals, etc.) within a medical treatment work-zone, or the like. In an embodiment, the right-staff verification device 120 includes one or more computing devices 112 that generate staff staging data based on at least one of the staff identification data, the staff authorization data, or the staff verification data. In an embodiment, the right-staff verification device 120 includes one or more computing devices 112 that generate staff staging data based on the patient-specific treatment staging data. In an embodiment, the right-staff verification device 120 includes one or more computing devices 112 that generate staff staging data based on the image data.

In an embodiment, a system 100 includes a right-staff verification device 120 configured to acquire image data of individuals within a medical treatment work-zone. In an embodiment, a system 100 includes a right-staff verification device 120 configured to determine at least one of staff identification data, staff authorization data, or staff verification data of the individuals based on the image data. In an embodiment, a system 100 includes a right-staff verification device 120 configured to generate patient-specific staff staging data. In an embodiment, a system 100 includes a right-staff verification device 120 configured to determine whether the right patient is about to be treated, whether the right treatment staff is present, whether the right instruments and equipment are present, whether the right location of the patient is being prepared for treatment, or the like, according to, for example, the patient-specific staff staging data, a standard treatment staging plan, or the like. In an embodiment, a system 100 includes a right-staff verification device 120 configured to track translation of at least one of an eye location or a hand location of at least one individual. In an embodiment, a system 100 includes a right-staff verification device 120 configured determine whether a treatment staging plan is being complied with by tracking translation of at least one of an eye location or a hand location of at least one individual within a treatment work-zone.

In an embodiment, a system 100 includes a right-staff verification device 120 configured to determine a proximity of the hand location or the eye location to at least one treatment work-surface 122 location. In an embodiment, a system 100 includes a right-staff verification device 120 configured to indicate, via one or more of a visual, audio, haptic, or a tactile representation, the proximity of the hand location or the eye location, to the at least one treatment work-surface 122 location. In an embodiment, a system 100 includes a right-staff verification device 120 configured to generate at least one of an audible warning, visual warning, electronic warning, or virtual warning indicative of the proximity of the hand location or the eye location to the at least one treatment work-surface 122 location. In an embodiment, a system 100 includes a right-staff verification device 120 configured to automatically enable or disable at least one of a medical apparatus 118 or a support equipment based on the proximity of the hand location or the eye location to the at least one treatment work-surface 122 location. In an embodiment, a system 100 includes a right-staff verification device 120 configured to automatically enable or disable at least one of a medical apparatus 118 (e.g., a surgical tool, surgical instrument, diagnostic equipment, support equipment, or the like) based whether a treatment staging plan compliance status.

In an embodiment, a system 100 includes a right-staff image recognition system 130. In an embodiment, a system 100 includes a right-staff image recognition system 130 configured to identify groups of pixels indicative of one or more individuals imaged in the at least one digital image, and to generate one or more connected components of a graph representative of groups of pixels indicative of the one or more individuals imaged in the at least one digital image.

In an embodiment, a system 100 includes a right-treatment object inventory recognition system 132.

In an embodiment, a medical apparatus 118 includes a right-site verification device 134. In an embodiment, the system 100 includes a right-site verification device 134. For example, in an embodiment, the system 100 includes a right-site verification device 134 configured to generate work-zone staging registration data associated with at least one of a patient treatment locality, an operation room staff work-region, or treatment work-surface locality 122. In an embodiment, the system 100 includes a right-site verification device 134 configured to acquire treatment plan data and at least one of identification data or authorization data from a medical procedure authorization device 104 associated with a patient. In an embodiment, the system 100 includes a right-site verification device 134 configured to generate treatment staging data consistent with the treatment plan data. For example, in an embodiment, the system 100 includes a right-site verification device 134 including one or more computing devices 112 that compare the generated work-zone staging registration data to patient-specific treatment staging data associated with a patient under treatment.

In an embodiment, the right-site verification device 134 is configured to generate at least one indicium of a physical location of the medical apparatus 118 respective to a treatment work-surface 122 location. In an embodiment, the right-site verification device 134 is configured to generate at least one indicium of a physical location of the medical apparatus 118 respective to a medical procedure authorization device 104 location. In an embodiment, the indicium includes generating at least one virtual object on a display representative of a locality of a treatment work-surface 122 respective to the medical apparatus 118. In an embodiment, the indicium includes generating at least one virtual object on a display representative of a locality of the medical apparatus 118 in reference to a treatment work-surface 122 associated with the patient-specific treatment staging data. In an embodiment, the right-site verification device 134 is configured to generate a virtual representation 146 of the medical apparatus 118 in a virtual space corresponding to the physical location of the medical apparatus 118 respective to a treatment work-surface 122 location.

In an embodiment, the right-site verification device 134 is operable to connect to a network. In an embodiment, the right-site verification device 134 is operable to connect to a local area network (LAN), a wide area network (WAN), and/or other networks. In an embodiment, the right-site verification device 134 is operable to connect to an enterprise-wide computer network, an enterprise-wide intranet, the Internet, or the like.

In an embodiment, the system 100, the medical apparatus 118, the right-site verification device 134, or the like operate in a cloud computing environment including one or more cloud computing systems (e.g., private cloud computing systems, public cloud computing systems, hybrid cloud computing systems, or the like.)

In an embodiment, the right-site verification device 134 includes one or more computing devices 112 that generate medical treatment work-zone staff staging data (e.g., surgery room staff staging data, provider staff staging data, treatment locality staff staging data, outpatient facility staff staging data, etc.) consistent with a treatment plan for the patient being treated. In an embodiment, the right-site verification device 134 includes one or more computing devices 112 that generate one or more cryptographic keys, based on the surgery room staff staging data, which provide authorization to the system 100, the medical apparatus 118, or the like to initiate treatment. In an embodiment, the right-site verification device 134 includes an irradiation authorization component that generates one or more cryptographic keys that provide authorized surgical procedure information to the medical apparatus 118. In an embodiment, the right-site verification device 134 includes an irradiation authorization component that informs the medical apparatus 118 to initiate treatment.

In an embodiment, the right-site verification device 134 is operable to communicate an authorization signal to the medical apparatus 118 upon verification of at least one of the identification data, the authorization data, or the treatment plan data obtained from the medical procedure authorization device 104 associated with a patient. In an embodiment, the right-site verification device 134 is operable to communicate treatment locality data to the medical apparatus 118 upon verification of at least one of the identification data, the authorization data, or the treatment plan data obtained from the medical procedure authorization device 104 associated with a patient. In an embodiment, the right-site verification device 134 is operable to communicate treatment registration data to the medical apparatus 118 upon verification of at least one of the identification data, the authorization data, or the treatment plan data obtained from the medical procedure authorization device 104 associated with a patient.

In an embodiment, the right-site verification device 134 includes one or more sensors 114 that provide treatment locality information as a function of the location of the medical apparatus 118 with respect to at least one of a treatment area, a treatment work-surface 122, or a treatment staging location. In an embodiment, the emitted electromagnetic or accosting signal can be used to designate not just whether the patient being treated is the correct patient, but also whether the location being treated is the correct treatment location; this can be based on proximity to the transmitter (e.g., signal strength, propagation time, phase change, etc.), on relative values due to multiple transmitters, etc., or the like.

In an embodiment, the right-site verification device 134 actively monitors (e.g., detects, tracks, etc.) an anatomical target, treatment work-surface 122, treatment work-zone, or the like located using at least one of computerized axial tomography, fiber optic thermometry, infrared thermography, magnetic resonance imaging, magnetic resonance spectroscopy, microwave thermography, microwave dielectric spectroscopy, positron emission tomography, ultrasound reflectometry, spectroscopic imaging, visual imaging, infrared imaging, single photon emission computed tomography, or the like.

In an embodiment, the right-site verification device 134 includes a sensor 114 that detects a location of a peripheral vascular bed, a biological structure, etc. using one or more imaging modalities. Non-limiting examples of imaging modalities include computerized axial tomography, fiber optic thermometry, infrared thermography, magnetic resonance imaging, magnetic resonance spectroscopy, microwave thermography, microwave dielectric spectroscopy, positron emission tomography, ultrasound reflectometry, spectroscopic imaging, visual imaging, infrared imaging, single photon emission computed tomography, or the like. In an embodiment, right-site verification device 134 includes a sensor 114 that detects and tracks a location of a peripheral vascular bed relative to the movement of a medical apparatus 118 using one or more imaging modalities. In an embodiment, the right-site verification device 134 registers the one or more work-surface 122 regions with the at least one treatment work-zone based on a detected location of a peripheral vascular bed.

In an embodiment, the system 100 includes a right-object inventory device 132. In an embodiment, the system 100 includes a right-object inventory device 132 configured to determine at least one of object identification data, object location data, object operational data based on the work-zone staging registration data. In an embodiment, the system 100 includes a right-object inventory device 132 configured to determine whether an object within a medical treatment work-zone is of the right type, in the right location, in the right staging work-zone, etc., based on the work-zone staging registration data.

In an embodiment, the system 100 includes an object tracking system 140. For example, in an embodiment, the system 100 includes an object tracking system 140 for updating in real time an object virtual location 142 in a virtual space 144 corresponding to the physical location of the object in a physical operation room work-region. In an embodiment, the object tracking system 140 is configured to continuously track translation of an object relative to a treatment work-surface locality and update the work-zone staging registration data based on the translation of the object relative to the treatment work-surface locality. In an embodiment, the object tracking system 140 is configured to continuously track an overall physical location of the object relative to a treatment work-surface locality. In an embodiment, object tracking system 140 includes an optical recognition distributed sensor network that determines treatment plan compliance data based on continuously tracking an overall physical location of the object relative to a treatment work-surface locality.

In an embodiment, the object tracking system 140 is configured to generate a virtual representation 146 of the object in a virtual space 144 corresponding to the physical location of the object respective to a treatment work-surface locality. In an embodiment, the object tracking system 140 is configured to generate at least one virtual object 142 on a virtual display representative of a locality of a medical apparatus 118 in reference to a treatment work-surface 122 as determined from patient-specific treatment staging data. In an embodiment, the object tracking system 140 is configured to generate at least one virtual object 142 on a virtual display representative of identity 143a, location 143b, position 143c, and movement 143d of a body portion of the one or more participants. In an embodiment, the object tracking system 140 is configured to generate at least one virtual object 142 on a virtual display representative of work-zone staging registration data.

Figure 2:
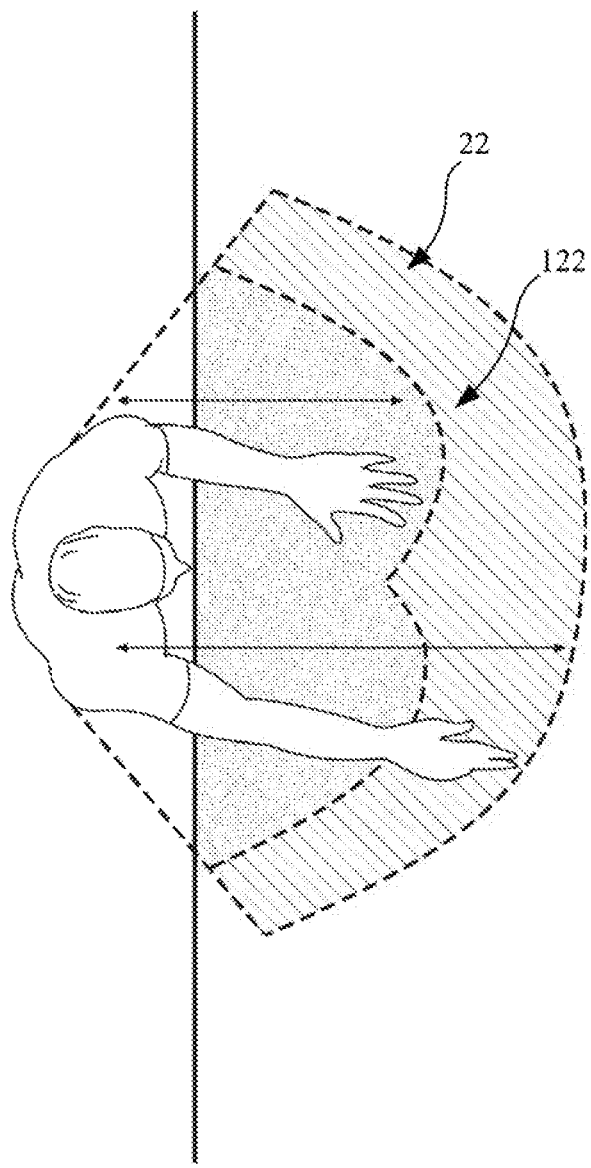
FIG. 2 is top-plan view of a work-volume registration system according to one embodiment.

In an embodiment, the system 100 includes a work-volume registration system 150. For example, in an embodiment, the system 100 includes a work-volume registration system 150 configured to track translation of a work-volume 222 associated with a medical practitioner, treatment staff, medical personnel, or the like (see e.g., FIG. 2). In an embodiment, the system 100 includes a work-volume registration system 150 configured to determine a proximity of the work-volume 222 to at least one treatment work-surface 122 location (e.g., treatment region, etc.) associated with a treatment staging plan. For example, in an embodiment, the system 100 includes a work-volume registration system 150 configured to determine a proximity of a work-volume 222 (e.g., a three-dimensional physical region bounded proximally by the body of the medical practitioner and distally by the arc swept by the fingertips of one or both hands with a range of elbow flexion or body rotations about its vertical axis, or the like) to at least one treatment work-surface 122 location (e.g., treatment region, etc.) associated with a treatment staging plan.

In an embodiment, the work-volume 222 comprises a three-dimensional physical region bounded proximally by the body of the medical practitioner and distally by the arc swept by the fingertips of one or both hands with a range of elbow flexion or body rotations about its vertical axis. In an embodiment, the work-volume 222 comprises a physical region bounded proximally by a proximal reach of the medical practitioner and by the distal boundary in any direction which the medical practitioner can attain by any combination of postures, rotations, flexion movements, or extension movements. In an embodiment, the work-volume 222 comprises a region defined by the reach of, for example, the medical practitioner.

In an embodiment, the work-volume registration system 150 is configured to generate registration data for aligning the work-volume 222 to at least one treatment work-zone consistent with the treatment staging plan. In an embodiment, the work-volume registration system 150 includes one or more computing devices 112 configured to generate a virtual representation 146 of the work-volume 222 associated with a medical practitioner in a virtual space corresponding to the physical location of the work-volume 222 respective to a treatment work-surface 122 location.

In an embodiment, the system 100 includes a real-time registration device 160. In an embodiment, the system 100 includes a real-time registration device 160 configured to register at least one work-volume 222 associated with a medical practitioner with at least one treatment work-zone and to generate work-zone registration information.

In an embodiment, the real-time registration device 160 registers a work-volume 222 with a treatment work-zone (e.g., a treatment focal area, a treatment focal zone, a treatment focal region, a treatment focal volume, a treatment target, a work surface, or the like) using one or more registration techniques or methodologies. For example, during operation, the real-time registration device 160 maps (e.g., spatially aligns, etc.) a work-volume 222 associated with a medical practitioner to a treatment work-zone. In an embodiment, the real-time registration device 160 registers a plurality of objects by mapping coordinates from one object to corresponding points in another object. In an embodiment, the real-time registration device 160 registers objects (e.g., working volumes and treatment work-zones, medical apparatuses 118 and work surfaces, target and reference objects, targets and focal regions, images, etc.) using one or more transformations.

Non-limiting examples of registration techniques or methodologies include deformable registration, landmark-based registration, or rigid registration. See e.g., Paquin et al., *Multiscale Image Registration*, Mathematical Biosciences and Engineering, Vol. 3:2 (2006); see also Paquin, Dana, PhD, *Multiscale Methods for Image Registration*, Ph.D. dissertation, Stanford University (2007); Zitova et al., *Image Registration Methods: a Survey*, Image and Vision Computing (21) pp. 977-1000 (2003); each of which is incorporated herein by reference. In an embodiment, registration includes techniques or methodologies for spatially aligning images taken using different imaging modalities, taken at different times, or that vary in perspective. Further non-limiting examples of registration techniques or methodologies include deformable multiscale registration, hybrid multiscale landmark registration, multiscale image registration, or rigid multiscale registration. In an embodiment, registration includes one or more of feature detection, feature identification, feature matching, or transform modeling. In an embodiment, registration includes mapping features of a first object with the features of a second object. In an embodiment, registration includes determining a point-by-point correspondence between two objects (e.g., a treatment focal region and a treatment target, etc.).

In an embodiment, the real-time registration device 160 includes one or more sensors 114 configured to detect one or more surface markings on a patient. In an embodiment, the real-time registration device 160 is configured to generate treatment work-zone registration data for registering of at least one work-volume 222 with at least one treatment work-zone relative to the detected one or more surface markings. In an embodiment, the real-time registration device 160 includes one or more sensors 114 configured to detect one or more surface markings on a patient and to generate registration data for registering the work-volume 222 with at least one treatment work-zone located using at least one of an anatomical target, a biological structure, an artificial surface marking, a tattoo, or a plurality of nanoparticle fiducial markers. In an embodiment, the real-time registration device 160 includes one or more sensors 114 configured to detect one or more odorant agents on a patient and to generate registration data for registering a work-volume 222 with at least one treatment work-zone located using the one or more odorant agents. In an embodiment, the real-time registration device 160 includes one or more sensors 114 configured to detect a treatment area boundary (operative site boundary) on a patient and to generate registration data for registering the work-volume 222 with at least one treatment work-zone located using the treatment area boundary. In an embodiment, a system 100 includes a right-treatment object inventory recognition system configured to identify groups of pixels indicative of one or more objects imaged in the at least one digital image, and to generate one or more connected components of a graph representative of groups of pixels indicative of an identity and locality of the one or more objects imaged in the at least one digital image.

In an embodiment, the right site, right-patient, determination system includes a real-time object and participant-recognition device. In an embodiment, a right-site, right-patient, determination system includes a real-time object and participant-recognition device including an optical recognition distributed sensor network that determines identity data associated with one or more participants and determines one or more of identity, location, position, or movement of a body portion of the one or more participants. In an embodiment, a right-site, right-patient, determination system using real-time automatic image recognition includes a real-time object recognition device. In an embodiment, a right-site, right-patient, determination system using real-time automatic image recognition includes a real-time object recognition device configured to identify groups of pixels indicative of one or more patient landmarks imaged in the at least one digital image.

In an embodiment, the a right-site, right-patient, determination system includes an optical recognition distributed sensor network that determines treatment plan compliance data based on one or more of the identity, location, position, or movement of a body portion of the one or more participants. In an embodiment, a right-site, right-patient, determination system using real-time automatic image recognition includes a real-time object recognition device configured to generate one or more connected components of a graph representative of groups of pixels indicative of the one or more one or more patient landmarks imaged in the at least one digital image.

In an embodiment, a right-site, right-patient, determination system using real-time automatic image recognition includes a real-time object recognition device configured to generate patient landmarks dynamics data indicative of at least one of an patient landmark position, patient landmark angle, patient landmark direction, patient landmark force, patient landmark contact, patient landmark pressure, patient landmark speed, patient landmark altitude, or patient landmark acceleration, or any combination thereof. In an embodiment, a right-site, right-patient, determination system using real-time automatic image recognition includes one or more pressure sensors configured to acquire measurand data from a medical apparatus 118 indicative of a presence of a patient proximate the medical apparatus 118.

Figure 3:
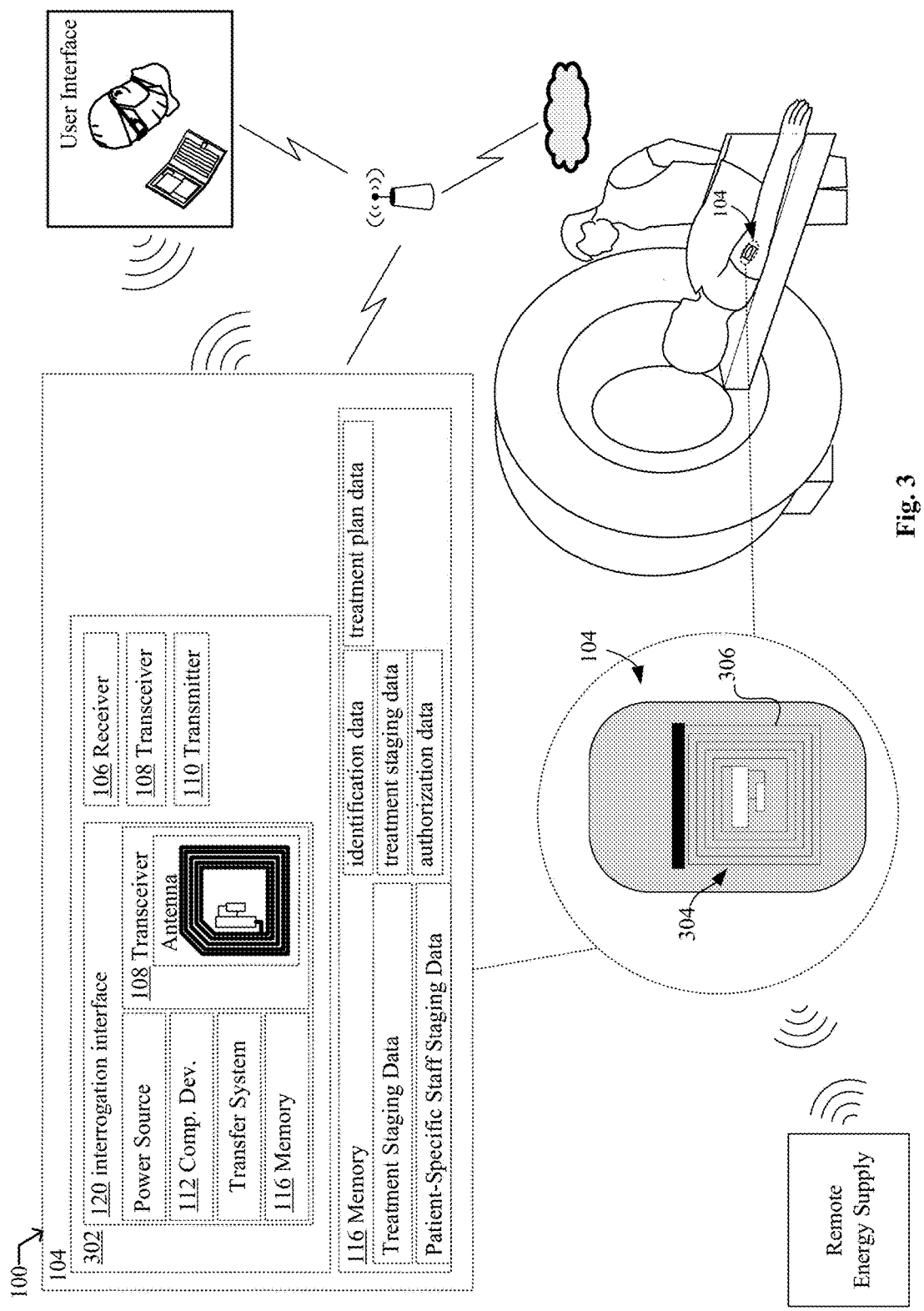
FIG. 3 is a perspective view of a medical procedure authorization system according to one embodiment

Referring to FIG. 3, in an embodiment, a medical procedure authorization device 104 includes a telematic right-site and right-patient verification device 302. In an embodiment, the telematic right-site and right-patient verification device 302 is configured to transmit a response signal corresponding to patient-specific treatment staging data when at least one of a wireless network access point, a Wi-Fi network, or wireless carrier network is detected. For example, in an embodiment, the telematic right-site and right-patient verification device 302 includes a transceiver operable to concurrently or sequentially transmit or receive one or more of the patient-specific treatment staging data, the patient-specific identification data, the patient-specific authorization data, or the patient-specific treatment plan data.

In an embodiment, the telematic right-site and right-patient verification device 302 transmits a response signal corresponding to the patient-specific treatment staging data responsive to interrogation of the telematic interface that satisfies response-selective criteria. In an embodiment, the telematic right-site and right-patient verification device 302 transmits one or more parameters associated with the patient-specific identification data, the patient-specific authorization data, or the patient-specific treatment plan data responsive to interrogation of the telematic interface that satisfies response-selective criteria. In an embodiment, the telematic right-site and right-patient verification device 302 is operable to establish a communication link with a medical apparatus 118 and to provide one or more of the patient-specific treatment staging data, the patient-specific identification data, the patient-specific authorization data, or the patient-specific treatment plan data to the medical apparatus 118. In an embodiment, the telematic right-site and right-patient verification device 302 includes one or more sensors 114 that determine proximity data (e.g., signal strength, propagation time, phase change, etc.) indicative of a medical apparatus 118 location relative to the medical procedure authorization device 104.

In an embodiment, a medical procedure authorization device 104 includes one or more memory devices 116 having patient-specific treatment staging data and at least one of patient-specific identification data, patient-specific authorization data, or patient-specific treatment plan data stored thereon. In an embodiment, a medical procedure authorization device 104 includes a telematic interface operable to communicate patient-specific treatment staging data and at least one of the patient-specific identification data, the patient-specific authorization data, or the patient-specific treatment plan data.

In an embodiment, the medical procedure authorization device 104 includes at least one receiver 106, transceiver 108, or transmitter 110 operable to concurrently or sequentially transmit or receive patient-specific treatment staging data. For example, in an embodiment, the implantable radiation sensing device 102 includes at least one receiver 106, transceiver 108, or transmitter 110 operable to concurrently or sequentially transmit or receive one or more of the patient-specific identification data, the patient-specific authorization data, or the patient-specific treatment plan data.

In an embodiment, the medical procedure authorization device 104 includes an interrogation interface 304. In an embodiment, the interrogation interface 304 is operably coupled to medical apparatus 118. In an embodiment, the interrogation interface 304 includes at least one bistatic antenna 306. In an embodiment, the interrogation interface 304 includes a carrier waveform selective interrogation interface. In an embodiment, the interrogation interface 304 includes a frequency selective interrogation interface. In an embodiment, the interrogation interface 304 includes an electromagnetic energy selective interrogation interface.

FIG. 4 shows a right-patient, right-procedure, verification method 400. At 410, the right-patient, right-procedure, verification method 400 includes eliciting at least one of identification data, authorization data, or treatment plan data from a medical procedure authorization device 104 associated with a patient. At 420, the right-patient, right-procedure, verification method 400 includes generating patient-specific treatment staging data consistent with the at least one of the identification data, the authorization data, or the treatment plan data. At 430, the right-patient, right-procedure, verification method 400 includes acquiring image data of individuals within a medical treatment work-zone. At 440, the right-patient, right-procedure, verification method 400 includes determining at least one of staff identification data, staff authorization data, or staff verification data of the individuals based on the image data. At 450, the right-patient, right-procedure, verification method 400 includes generating at least one virtual object on a virtual display representative of a physical locality of a medical staff member in reference to a treatment work-surface 122 associated with the patient-specific treatment staging data.

Referring to FIGS. 5A and 5B, in an embodiment, an article of manufacture, an apparatus (e.g., a medical apparatus 118, etc.), or the like, includes a computer program product 502 including a signal-bearing medium bearing one or more instructions for establishing surgery room staff staging data consistent with a treatment plan for the patient. In an embodiment, the computer program product 502 includes a non-transitory signal-bearing medium bearing one or more instructions for establishing treatment instrumentation staging data consistent with the treatment plan for the patient. In an embodiment, the computer program product 502 includes a non-transitory signal-bearing medium bearing one or more instructions for generating a virtual representation 146 of the medical apparatus 118 in a virtual space corresponding to the physical location of the medical apparatus 118 respective to a treatment work-surface 122 location. In an embodiment, the computer program product 502 includes a non-transitory signal-bearing medium bearing one or more instructions for generating one or more cryptographic keys, based on the surgery room staff staging data, which provide authorization to the medical apparatus 118 to initiate treatment.

In an embodiment, an article of manufacture, an apparatus (e.g., a medical apparatus 118, etc.), or the like, includes a computer program product 502 including a non-transitory signal-bearing medium bearing one or more instructions for detecting the presence and identity of at least one operating theater staff member. In an embodiment, the computer program product 502 includes a non-transitory signal-bearing medium bearing one or more instructions for determining the physical location of the operating theater staff member relative to a treatment work-surface 122. In an embodiment, the computer program product 502 includes a non-transitory signal-bearing medium bearing one or more instructions for registering the physical location of the operating theater staff member relative to the treatment work-surface 122. In an embodiment, the computer program product 502 includes a non-transitory signal-bearing medium bearing one or more instructions for initiating a discovery and a registration protocol that allows the medical procedure authorization device 104 and the medical apparatus 118 to find each other and negotiate one or more pre-shared keys.

In an embodiment, the computer program product 502 includes a non-transitory signal-bearing medium bearing one or more instructions for registering a treatment staging position location with the physical location of the operating theater staff member based on patient specific treatment staging data. In an embodiment, the computer program product 502 includes a non-transitory signal-bearing medium bearing one or more instructions for detecting the presence and identity of at least one treatment instrument. In an embodiment, the computer program product 502 includes a non-transitory signal-bearing medium bearing one or more instructions for determining the physical location of the treatment instrument relative to the treatment work-surface 122. In an embodiment, the computer program product 502 includes a non-transitory signal-bearing medium bearing one or more instructions for actuating a system 100 to track translation of one or more treatment instrument relative to the treatment work-surface 122

In an embodiment, the computer program product 502 includes a non-transitory signal-bearing medium bearing one or more instructions for registering the physical location of the treatment instrument relative to the treatment work-surface 122. In an embodiment, the computer program product 502 includes a non-transitory signal-bearing medium bearing one or more instructions for registering a treatment staging position location with the physical location of the treatment instrument based on patient specific treatment staging data. In an embodiment, the computer program product 502 includes a non-transitory signal-bearing medium bearing one or more instructions for registering a patient location with the physical location of the treatment instrument based on patient specific treatment staging data.

In an embodiment, the computer program product 502 includes a non-transitory signal-bearing medium bearing one or more instructions for telemetrically acquiring at least one of identification data, authorization data, or treatment plan data from a medical procedure authorization device 104 associated with a patient. In an embodiment, the computer program product 502 includes a non-transitory signal-bearing medium bearing one or more instructions for generating patient-specific treatment staging data. In an embodiment, the computer program product 502 includes a non-transitory signal-bearing medium bearing one or more instructions for acquiring image data of individuals within a medical treatment work-zone.

In an embodiment, the computer program product 502 includes a non-transitory signal-bearing medium bearing one or more instructions for determining at least one of staff identification data, staff authorization data, or staff verification data of the individuals based on the image data. In an embodiment, the computer program product 502 includes a non-transitory signal-bearing medium bearing one or more instructions for determining a locality of one or more individuals within the medical treatment work-zone in reference to a medical treatment work-zone based on the image data. In an embodiment, the computer program product 502 includes a non-transitory signal-bearing medium bearing one or more instructions for generating a virtual representation 146 of the locality of the one or more individuals within the medical treatment work-zone on a virtual display based on at least one of the staff identification data, the staff authorization data, or the staff verification data. In an embodiment, the computer program product 502 includes a non-transitory signal-bearing medium bearing one or more instructions for generating health record data based on the patient-specific treatment staging data.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for detecting position and/or velocity, control motors for moving and/or adjusting components and/or quantities). A data processing system can be implemented utilizing suitable commercially available components, such as those typically found in data computing/communication and/or network computing/communication systems.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware in one or more machines or articles of manufacture), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation that is implemented in one or more machines or articles of manufacture; or, yet again alternatively, the implementer may opt for some combination of hardware, software, and/or firmware in one or more machines or articles of manufacture. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware in one or more machines or articles of manufacture.

The herein described subject matter sometimes illustrates different components contained within, or connected with, different other components. It is to be understood that such depicted architectures are merely examples, and that in fact, many other architectures can be implemented that achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably coupleable," to each other to achieve the desired functionality. Specific examples of operably coupleable include, but are not limited to, physically mateable and/or physically interacting components, and/or wirelessly interactable, and/or wirelessly interacting components, and/or logically interacting, and/or logically interactable components.

In an embodiment, one or more components may be referred to herein as "configured to," "configurable to," "operable/operative to," "adapted/adaptable," "able to," "conformable/conformed to," etc. Such terms (e.g., "configured to") can generally encompass active-state components and/or inactive-state components and/or standby-state components, unless context requires otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by the reader that each function and/or operation within such block diagrams, flowcharts, or examples can be implemented, individually and/or collectively, by a wide range of hardware, software, firmware in one or more machines or articles of manufacture, or virtually any combination thereof. Further, the use of "Start," "End," or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application. In an embodiment, several portions of the subject matter described herein is implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal-bearing medium used to actually carry out the distribution. Non-limiting examples of a signal-bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., receiver 106, transceiver 108, transmitter 110, transmission logic, reception logic, etc.), etc.).

While particular aspects of the present subject matter described herein have been shown and described, it will be apparent to the reader that, based upon the teachings herein, changes and modifications can be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the operations recited therein generally may be performed in any order. Also, although various operational flows are presented in a sequence(s), it should be understood that the various operations may be performed in orders other than those that are illustrated, or may be performed concurrently. Examples of such alternate orderings includes overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A medical system, comprising:
   a right-patient verification device having an interrogation interface device configured to elicit at least one of identification data, authorization data, or treatment plan data from a medical procedure authorization device associated with a patient;
   a right-site verification device configured to generate patient-specific treatment staging data consistent with the at least one of the identification data, the authorization data, or the treatment plan data, the patient-specific treatment staging data including registration data for registering a work-volume associated with a medical practitioner to at least one treatment plan work zone consistent with a treatment plan for the patient, the registration data representing a spatial relationship between the work-volume and the at least one treatment plan work zone, the work-volume including at least a portion of a body of the medical practitioner and a region within which the medical practitioner can extend at least one limb; and
   a work-volume registration system configured to track the spatial relationship between the work-volume and the at least one treatment plan work zone independently of a surgical instrument while the work-volume and the at least one treatment plan work zone are nonoverlapping.

2. The medical system of claim 1, wherein the right-patient verification device includes at least one acoustic energy transmitter or electromagnetic energy transmitter.

3. The medical system of claim 1, wherein the right-patient verification device includes at least one of a carrier waveform selective interrogation interface or a frequency selective interrogation interface.

4. The medical system of claim 1, wherein the right-patient verification device includes at least one of an acoustic energy selective interrogation interface or an electromagnetic energy selective interrogation interface.

5. The medical system of claim 1, wherein the right-site verification device is configured to generate at least one indicium of a physical location of a medical apparatus respective to a treatment work-surface location.

6. The medical system of claim 5, wherein the indicium includes generating at least one virtual object on a display representative of a locality of a treatment work-surface respective to the medical apparatus.

7. The medical system of claim 5, wherein the indicium includes generating at least one virtual object on a display representative of a locality of the medical apparatus in reference to a treatment work-surface associated with the patient-specific treatment staging data.

8. The medical system of claim 1, wherein the right-site verification device is configured to generate a virtual representation of the medical apparatus in a virtual space corresponding to the physical location of the medical apparatus respective to a treatment work-surface location.

9. The medical system of claim 1, wherein the right-site verification device is operable to connect to a network.

10. The medical system of claim 1, further comprising:
a computer program product including a signal-bearing medium bearing
one or more instructions for generating medical treatment work-zone staff staging data consistent with a treatment plan for the patient;
one or more instructions for generating treatment instrumentation staging data consistent with the treatment plan for the patient; and
one or more instructions for generating a virtual representation of the medical apparatus in a virtual space corresponding to the physical location of the medical apparatus respective to a treatment work-surface location.

11. The medical system of claim 10, further comprising:
a computer program product including a signal-bearing medium bearing
one or more instructions for generating one or more cryptographic keys, based on the medical treatment work-zone staff staging data, which provide authorization to the medical apparatus to initiate treatment.

12. The medical system of claim 1, further comprising: a network.

13. The medical system of claim 1, wherein the right-site verification device is operable to communicate an authorization signal to the medical apparatus upon verification of at least one of the identification data, the authorization data, or the treatment plan data obtained from the medical procedure authorization device associated with a patient.

14. The medical system of claim 1, wherein the right-site verification device is operable to communicate treatment locality data to the medical apparatus upon verification of at least one of the identification data, the authorization data, or the treatment plan data obtained from the medical procedure authorization device associated with a patient.

15. The medical system of claim 1, wherein the right-site verification device includes one or more sensors that provide treatment locality information as a function of the location of the medical apparatus with respect to at least one of a treatment area, a treatment work-surface, or a treatment staging location.

16. The medical system of claim 1 wherein the work-volume includes an upper portion of the body of the medical practitioner.

17. The medical system of claim 1 wherein the work-volume includes a region within which the medical practitioner can extend partially at least one limb.

18. The medical system of claim 1 wherein the work-volume includes a region within which the medical practitioner can extend fully at least one limb.

19. A medical procedure monitoring system, comprising:
a right-patient verification device configured to
acquire at least one of identification data, authorization data, or treatment plan data from a medical procedure authorization device associated with a patient, and
generate patient-specific treatment staging data, including first registration data associated with at least one treatment region for the patient;
a right-staff verification device including one or more sensors operable to detect individuals within a medical treatment work-zone, the right-staff verification device configured to
acquire image data of individuals within a medical treatment work-zone,
determine at least one of staff identification data, staff authorization data, or staff verification data of the individuals based on the image data, and
generate patient-specific staff staging data including second registration data for registering a work-volume associated with at least one non-patient individual within the medical treatment area to the at least one treatment region for the patient, the second registration data representing a spatial relationship between the work-volume and the at least one treatment region, the work-volume including at least a portion of a body of the at least one non-patient individual and a region within which the at least one non-patient individual can reach; and
a work-volume registration system configured to determine a proximity of the work-volume to the at least one treatment region while the work-volume is separate from the at least one treatment region and without tracking an object being held by the at least one non-patient individual.

20. The system of claim 19, wherein the right-patient verification device is further configured to:
determine patient identification by facial recognition.

21. The system of claim 19, wherein the right-patient verification device is further configured to:
determine patient identification based on image data associated with at least one of an anatomical target, a biological structure, an artificial surface marking, a tattoo, or a plurality of nanoparticle fiducial markers.

22. The system of claim 19, wherein the right-patient verification device is further configured to:
detect preparation to act on a body part or action in progress.

23. The system of claim 19, wherein the right-patient verification device is further configured to:
detect exposure of a body part.

24. The system of claim 19, wherein the right-patient verification device is further configured to:
detect application of antiseptic or sterilants in preparation for surgery.

25. The medical procedure monitoring system of claim 19 wherein the work-volume includes a torso of the body of the medical practitioner.

26. The medical procedure monitoring system of claim 19 wherein the work-volume includes a region within which the at least one of the non-patient individuals can reach partially.

27. The medical procedure monitoring system of claim 19 wherein the work-volume includes a region within which the at least one of the non-patient individuals can partially reach fully.

28. A medical system, comprising:
a right-site verification device configured to generate work-zone staging registration data associated with at least one of a patient treatment locality, an operation room staff work-region, or a treatment work-surface locality, the work-zone staging registration data including registration data for registering a work-volume associated with a medical practitioner to at least one of the patient treatment locality, the operation room staff work-region, or the treatment work-surface locality, the work-volume including at least a portion of a body of the medical practitioner and a region within which the medical practitioner can extend at least one hand; and a right-object inventory device configured to determine at least one of object identification data, object location data, or object operational data based on the work-zone staging registration data;

an object tracking system for updating in real time an object virtual location in a virtual space corresponding to the physical location of the object in a physical operation room work-region in which a patient is, or is to be, located; and a work-volume registration system configured to generate a work-volume virtual location in the virtual space corresponding to a physical location of the work-volume in the physical operation room work-region while the medical practitioner is not holding a tracked object.

29. The system of claim 28, wherein the object tracking system is configured to continuously track translation of an object relative to a treatment work-surface locality and update the work-zone staging registration data based on the translation of the object relative to the treatment work-surface locality.

30. The system of claim 28, wherein the object tracking system is configured to continuously track an overall physical location of the object relative to a treatment work-surface locality.

31. The system of claim 28, wherein the object tracking system is configured to generate at least one virtual object on a virtual display representative of a locality of a medical apparatus in reference to a treatment work-surface associated with the work-zone staging registration data.

32. The medical system of claim 28 wherein the work-volume includes a region within which the medical practitioner can extend partially at least one hand.

33. The medical system of claim 28 wherein the work-volume includes a region within which the medical practitioner can extend fully at least one hand.

34. A right-patient, right-procedure, verification method, comprising:

eliciting at least one of identification data, authorization data, or treatment plan data from a medical procedure authorization device associated with a patient;

generating patient-specific treatment staging data consistent with the at least one of the identification data, the authorization data, or the treatment plan data, the patient-specific treatment staging data including registration data for registering a work-volume associated with a medical practitioner to at least one treatment work-zone associated with a patient under treatment, the registration data representing a spatial relationship between the work-volume and the at least one treatment work-zone, the work-volume including at least a portion of a body of the medical practitioner and a region within which the medical practitioner can move consistent with a treatment staging plan;

tracking the spatial relationship while the work-volume is spaced apart from the at least one treatment work-zone whether or not the medical practitioner is associated with a medical instrument; and determining a treatment staging plan compliance status based on a registration of the work-volume to the at least one treatment work-zone.

35. The right-patient, right-procedure, verification method of claim 34, further comprising:

acquiring image data of individuals within a medical treatment work-zone.

36. The right-patient, right-procedure, verification method of claim 35, further comprising:

determining at least one of staff identification data, staff authorization data, or staff verification data of the individuals based on the image data.

37. The right-patient, right-procedure, verification method of claim 35, further comprising:

generating at least one virtual object on a virtual display representative of a physical locality of a medical staff member in reference to a treatment work-surface associated with the patient-specific treatment staging data.

38. The method of claim 34 wherein the work-volume includes a shoulder portion of the body of the medical practitioner.

39. The method of claim 34 wherein the work-volume includes a region within which the medical practitioner can extend partially at least one appendage.

40. The method of claim 34 wherein the work-volume includes a region within which the medical practitioner can extend fully at least one appendage.

* * * * *